United States Patent [19]

Waterman et al.

[11] Patent Number: 4,778,837
[45] Date of Patent: Oct. 18, 1988

[54] LOW BASICITY HINDERED AMINE LIGHT STABILIZERS

[75] Inventors: Paul S. Waterman, Shelton, Conn.; Frank F. Loffelman, Bridgewater, N.J.

[73] Assignee: American Cyanamid Company, Stamford, Conn.

[21] Appl. No.: 946,409

[22] Filed: Dec. 24, 1986

Related U.S. Application Data

[63] Continuation of Ser. No. 730,150, May 3, 1985, abandoned.

[51] Int. Cl.$^4$ .............................................. C08L 5/34
[52] U.S. Cl. ...................................... 524/89; 524/91; 524/94; 524/102; 524/103
[58] Field of Search ............... 524/89, 91, 94, 102, 524/103

[56] References Cited

U.S. PATENT DOCUMENTS 4,356,307 10/1982 Kelkenberg .................. 546/200
4,426,471 1/1984 Berner ........................ 524/100

Primary Examiner—Kriellion Morgan
Attorney, Agent, or Firm—Roger S. Benjamin

[57] ABSTRACT

A method of stabilizing an acid cured coating formulation against photo and/or thermal degradation without adverse effect on acid cure is disclosed. The method discloses incorporating a stabilizingly effective amount of a hindered amine light stabilizer (HALS) represented by Formula I:

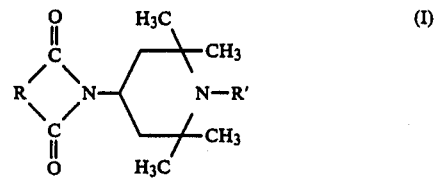

wherein R is a saturated or unsaturated, optionally alkyl- or alkenyl-substituted alkylene or cycloalkylene radical having 2-20 C-atoms and R' is selected from the group consisting of:
  hydrogen;
  an alkyl radical having 1-20 C-atoms;
  an alkenyl radical having 3-5 C-atoms;
  an aralkyl radical having 7-12 C-atoms;
  —$CH_2$—$CH_2$—CN;
  —$CH_2$—COO—alkyl;
  —$CH_2$—CH($CH_3$)—COO—alkyl; an acyl radical; and
  —($CH_2$—$CH_2$O)$_n$H, wherein n can be 1-10.

Also disclosed is an acid cured coating composition stabilized against photo and/or thermal degradation. The composition comprises: a stabilizingly effective amount of HALS represented by Formula I above.

17 Claims, No Drawings

LOW BASICITY HINDERED AMINE LIGHT STABILIZERS

This is a continuation of application Ser. No. 730,150, filed May 3, 1985, now abandoned.

FIELD

This invention relates to low basicity hindered amine light stabilizers (HALS).

BACKGROUND

HALS are well known in the art, especially those based on a tetraalkylpiperidine molecule (see for example U.S. Pat. No. 4,426,471 and U.S. Pat. No. 4,426,472). The HALS are utilized to stabilize polymeric substances against degradation due to, for example, light, particularly ultraviolet (UV) light. In some polymeric substances, such as coating formulations, an acidic curing agent is utilized to cure the coating composition. Utilization of basic HALS can adversely effect the cure of the coating by reacting with the acidic curing agent. Therefore, a desirable HALS for use in such circumstances would have as low a basicity as possible to reduce or eliminate interaction with the acid cure.

U.S. Pat. No. 4,356,307 discloses cyclic imides and their use as stabilizers for plastics, especially polyolefins, against photo and/or thermal degradation. The cyclic imides are represented by the general formula:

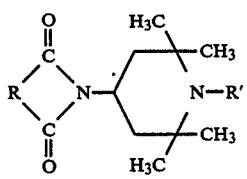

in which R represents a saturated or unsaturated, optionally alkyl- or alkenyl-substituted alkylene or cycloalkylene radical having 2–20 C-atoms and in which R' represents hydrogen or a substituent such as,
an alkyl radical having 1–20 C-atoms,
an alkenyl radical having 3–5 C-atoms,
an aralkyl radical having 7–12 C-atoms,
—CH$_2$—CH$_2$—CN,
—CH$_2$—CH$_2$—COO—alkyl,
—CH$_2$—CH(CH$_3$)—COO—alkyl,
an acyl radical or —(CH$_2$—CH$_2$O)$_n$H, wherein n can be 1–10.

Berner, G. and Rembold, M., "New Light Stabilizers for High-Solid Coatings", in: Parfit, G. D. and Partsis, A. V., *Organic Coatings, Science and Technology* (1984), pp. 55–85, TP 1175.S607, relates to the search for a HALS with low bascity for use with 1-package high-solid paints (see for example pp. 75 et. seq.).

U.S. Pat. No. 4,419,472 discloses ester mixtures of polyalkylpiperidine derivatives of the formulas:

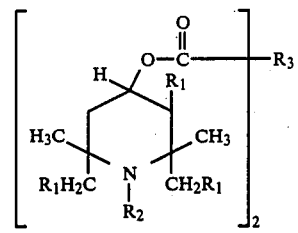

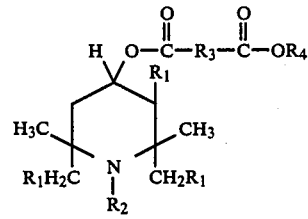

wherein R$_1$ is hydrogen or methyl, R$_2$ is hydrogen, C$_{1-12}$ alkyl, C$_{3-8}$ alkenyl, C$_{7-11}$ aralkyl, cyanomethyl or C$_{2-4}$ acyl, R$_3$ is C$_{1-18}$ alkylene, C$_{2-18}$ oxaalkylene, C$_{2-18}$ thiaalkylene, C$_{2-18}$ azaalkylene or C$_{2-8}$ alkenylene and R$_4$ is C$_{1-4}$ alkyl. These mixtures are disclosed as being suitable as stabilizers for plastics.

A significant contribution to the art would be a method for stabilizing a polymeric substrate, such as an acid catalyzed coating formulation, utilizing a HALS which has little or no effect on the cure (as measured by the Knoop hardness test). Such a contribution is provided by this invention.

SUMMARY OF THE INVENTION

It has surprisingly been discovered that there is little or no effect on the hardness (Knoop) of acid cured coating compositions when HALS represented by Formula I are utilized to provide stabilization against photo and/or thermal degradation:

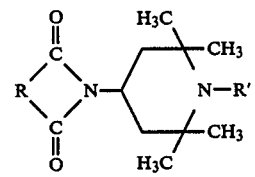

(I)

wherein R represents a saturated or unsaturated, optionally alkyl- or alkenyl-substituted alkylene or cycloakylene radical having 2–20 C-atoms and in which R' represents hydrogen or a substituent such as,
an alkyl radical having 1–20 C-atoms,
an alkenyl radical having 3–5 C-atoms,
an aralkyl radical having 7–12 C-atoms,
—CH$_2$—CH$_2$—CN,
—CH$_2$CH$_2$—COO—alkyl,
—CH$_2$—CH(CH$_3$)—COO—alkyl,
an acyl radical or —(CH$_2$—CH$_2$O)$_n$H, wherein n can be 1–10.

This is quite unexpected because based on the structure alone, the non-adverse effect of the HALS of Formula I in acid cured coating compositions could not be predicted.

DETAILED DESCRIPTION OF THE INVENTION

This invention provides a method of stabilizing an acid catalyzed coating formulation against photo and/or thermal degradation comprising incorporating in said coating formulation a stabilizingly effective amount of a HALS represented by Formula I:

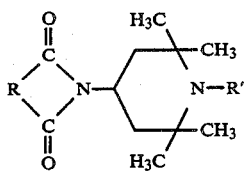

wherein R represents a saturated or unsaturated, optionally alkyl- or alkenyl-substituted alkylene or cycloalkylene radical having 2-20 C-atoms and in which R' represents hydrogen or a substituent such as,

- an alkyl radical having 1-20 C-atoms with methyl being preferred,
- an alkenyl radical having 3-5 C-atoms,
- an aralkyl radical having 7-12 C-atoms,
- $-CH_2-CH_2-CN$,
- $-CH_2-CH_2COO-$alkyl,
- $-CH_2-CH(CH_3-COO-$alkyl,
- an acyl radical or $-(CH_2-CH_2O)_nH$, wherein n can be 1-10.

Another embodiment of this invention provides an acid cured coating composition stabilized against photo and/or thermal degradation comprising a stabilizingly effective amount of a HALS represented by the formula I:

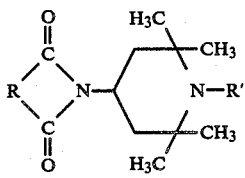

wherein R represents a saturated or unsaturated, optionally alkyl- or alkenyl-substituted alkylene or cycloalkylene radical having 2-20 C-atoms and in which R' represents hydrogen or a substituent such as,

- an alkyl radical having 1-20 C-atoms,
- an alkenyl radical having 3-5 C-atoms,
- an aralkyl radical having 7-12 C-atoms,
- $-CH_2-CH_2CN$,
- $-CH_2-CH_2-COO-$alkyl,
- $-CH_2-CH(CH_3)-COO-$alkyl,
- an acyl radical or $-(CH_2O)_nH$, wherein n can be 1-10.

The acid cured coating formulations can comprise any of the known conventional coating compositions. Examples include, but are not limited to, solvent- or water-based acrylic lacquers, acrylic dispersion lacquers, solvent- or water-based thermosetting acrylic enamels, polyester enamels, non-aqueous acrylic dispersion enamels, alkyd resin enamels, polyurethane enamels, acrylic or polyester powder coatings, and the like.

Preferred coating compositions are acid catalyzed thermoset acrylic or alkyd coatings. Coating compositions utilizable in this invention are described in detail in U.S. Pat. No. 4,355,071, the disclosure of which is incorporated herein by reference.

The acid curative utilized is any of those already known to the art for the aforementioned coating compositions. For example, substituted or un-substituted alkyl sulfonic acids, aryl sulfonic acids, phosphonic acids, phosphinic acids, benzenephosphonic acid, and the like. Preferably toluenesulfonic acid is used.

In the HALS represented by Formula I, R is preferably a group represented by Formulas II and III:

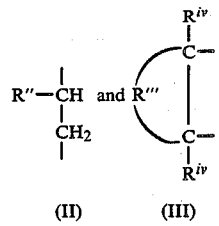

In Formula II, R'' is selected from the group consisting of: (a) $C_{12}-C_{18}$ alkyl or alkylene; (b) cycloalkylene; (c) 1,2-cyclohexanediyl and methyl-substituted 1,2-cyclohexanediyl radicals; and (d) bicyclic divalent radicals. Such compounds are described in detail in U.S. Pat. No. 4,356,307, the disclosure of which is incorporated herein by reference.

In Formula III, R''' is a ring or ring system, for example an alicyclic ring and preferably a bicyclic ring, and $R^{iv}$ is hydrogen or alkyl.

Examples of groups of Formula III include but are not limited to the following:

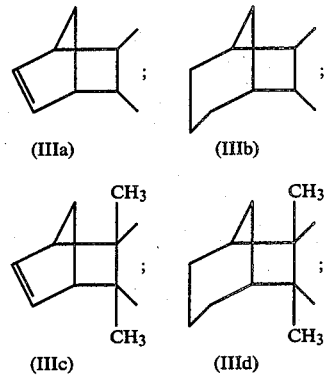

(IIIa); (IIIb); (IIIc); (IIId)

Therefore, when R is a group of Formula III, representative examples of compounds of Formula I include:

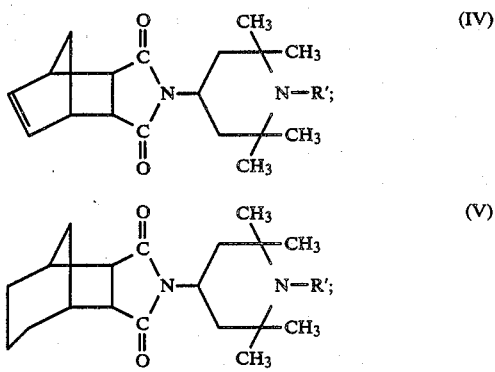

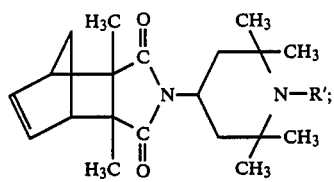

(VI)

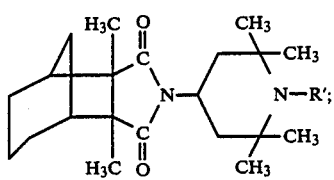

(VII)

and the like.

Other ring or ring systems which may prove useful for R''' are mononuclear aromatic rings. The mononuclear aromatic rings may have cyclic imides bound to their nucleus and these cyclic imides may further be bound to the 4-position of a 2,2,6,6-tetramethylpiperidine molecule. Thus, compounds of Formula I derived from such substituents may include those represented by:

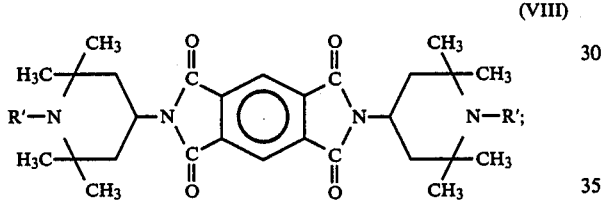

(VIII)

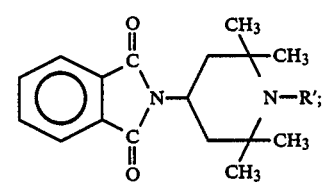

(IX)

and the like.

Additional ring or ring systems which may prove useful for R''' include alicyclic rings which are bound to the nucleus of a mononuclear aromatic cyclic imide which is bound to the 4-position of a 2,2,6,6-tetramethylpiperidine molecule. Compounds of Formula I derived from such substituents may include those represented by:

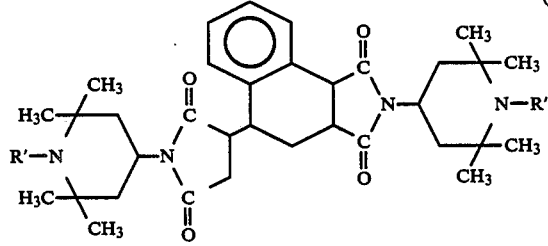

(X)

and the like.

Most preferably R of Formula I is a group of Formula II and still more preferably R is a group selected from the group consisting of:

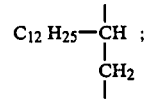

(XI)

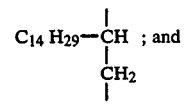

(XII)

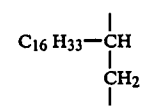

(XIII)

Thus, the more preferred HALS of Formula I are:

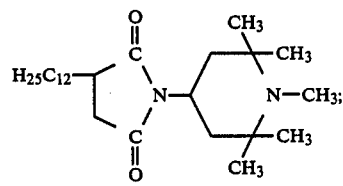

(XIV)

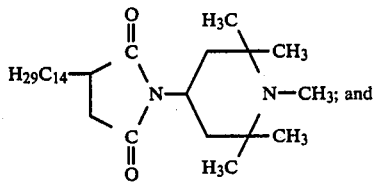

(XV)

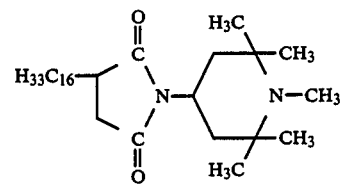

(XVI)

In Formulas IV–X and XIV–XVI R' is as defined for Formula I.

In general, at least about 0.1–5.0 wt. % of the HALS, based on the weight of resin solids, is used, with about 0.5% to about 1.5% wt. % being preferred.

Other stabilizers may be incorporated into the coating compositions. These stabilizers may include for example:

Antioxidants—such as alkylated monophenols, alkylated hydroquinones, hydroxylated thiodiphenyl ethers, alkylidene-bisphenols, benzyl compounds, acylaminophenols, esters of β-(3,5-di-tert-butyl-4-hydroxyphenyl)propionic acid with monohydric or polyhydric alcohols, esters of β-(5-tert-butyl-4-hydroxy-3-methylphenyl)-propionic acid with monohydric or polyhydric alcohols, and amides of β-(3,5-di-tert-butyl-4-hydroxyphenyl)propionic acid;

UV absorbers and light stabilizers—such as 2-(2'-hydroxyphenyl)-benzotriazoles, 2-hydroxybenzophenonesesters of substituted and unsubstituted benzoic acids, acrylates, nickel compounds, and oxalic acid dianilides;

Metal deactivators;

Phosphites and phosphonites;
Compounds which decompose peroxide;
Polyamide stabilizers;
Basic co-stabilizers;
Nucleating agents;
Fillers and reinforcing agents; and
Other additives—such as plasticizers, lubricants, emulsifiers, pigments, fluorescent whitening agents, flameproofing agents, antistatic agents and blowing agents.

These stabilizers are described in U.S. Pat. No. 4,419,472 the disclosure of which is incorporated herein by reference.

The following examples are provided for the purposes of illustration only. The examples should not be construed as limiting the invention in any way as variations of the invention are possible which do not depart from the spirit and scope of the appended claims.

TEST PROCEDURES

In the following examples, the effects of different HALS on the cure of a coating was determined by measuring the hardness of the cured coating. The hardness was determined by Knoop Indentation Hardness (Knoop or KHN), ASTM D-1474, Method A.

BASIC COATING FORMULATION

In the following examples, coating formulation and procedure was as follows, unless indicated otherwise.

13.0 parts TSA resin ACRYLOID ®At-400 brand of thermosetting acrylics resin (a trademark of Rohm & Hass Co.) (75% solids).

5.25 parts CYMEL ®303 brand of melamine resin (a trademark of American Cyanamid Co.).

0.15 parts TSA catalyst CYCAT ®4040 brand of p-toluene sulfonic acid (a trademark of American Cyanamid Co.) (40% in isopropanol).

3.3 parts Xylene.
3.3 parts butanol.
0.15 parts HALS, 1% on total resin solids.

The formulations were coated onto BONDERITE ®40 brand of cold rolled steel test panels (Parker-Div.-Hooker Chemical and Plastics Corporation) and cured for 30 minutes at 120° C. After conditioning at 25° C. and 50% relative humidity for 24 hours, hardness measurements were made. Thickness of the cured coating was about 2 mils.

The HALS used in the following examples were:

HALS 1

A mixture of:

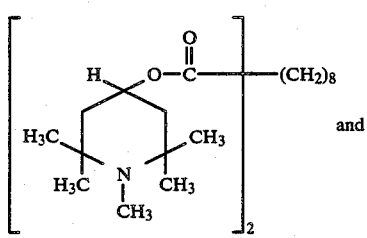

(XVII)

and

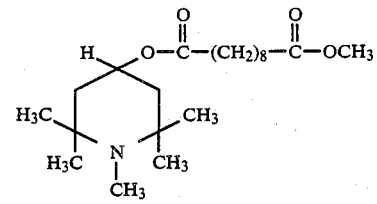

(XVIII)

HALS 2

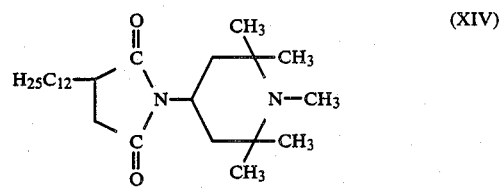

(XIV)

HALS 3

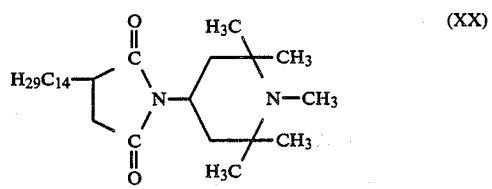

(XX)

HALS 4

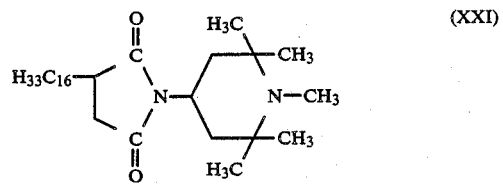

(XXI)

HALS 5

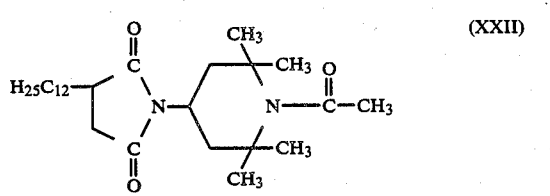

(XXII)

HALS 6

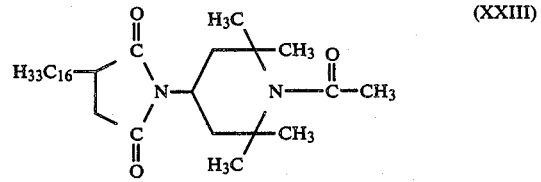

(XXIII)

Preparation of HALS 1-6

HALS 1

This mixture is commercially available from Ciba-Geigy Corporation as TINUVIN®765 brand of HALS.

HALS 2

A solution containing 10 parts of the compound of Formula I wherein R is a group of Formula XI and R'=H, 7.8 parts of formic acid and 15.3 parts of 37% formaldehyde solution was refluxed for 18 hours. After cooling to 30° C., 40 parts of methylene chloride and 5N-sodium hydroxide solution was added until the pH of the solution was >10. The organic layer was dried over $K_2CO_3$ and the solvent removed yielding 8.5 parts of product as a slightly yellow oil.

HALS 3

The same procedure used for HALS 2 was followed except that a compound of Formula XII was used.

HALS 4

The same procedure used for HALS 2 was followed except that a compound of Formula XIII was used.

HALS 5

A solution containing 10 parts of the compound of Formula I wherein R is a group of Formula XI and R'=H and 20 parts of acetic anhydride was refluxed for 7 hours. The excess anhydride and acetic acid was then removed under vacuum yielding 10.25 parts of product.

HALS 6

The same procedure used for HALS 5 was followed except that a compound of Formula XII was used. A yield of 10.5 parts of product was obtained.

APPLICATION

Example 1

HALS 1-4 were utilized in the basic coating formulation and tested for their effect on cure at 120° C. Table I reports the Knoop hardness (KHN) of the coating obtained with these HALS.

TABLE I

| Effect on Cure of HALS 1-4 | |
|---|---|
| HALS | KHN* |
| None | 7.8 |
| 1 | 0.7 |
| 2 | 7.8 |
| 3 | 7.5 |
| 4 | 6.7 |

*Knoop Hardness No. (25 g wgt. - 10 × Power)

The data shown in Table I demonstrates that HALS 2-4 of this invention have little or no effect on the cure of the coating. However, in comparison, HALS 1 greatly affects the cure.

Example 2

HALS 5 and 6 were utilized in the basic coating formulation and tested for their effect on cure. These coatings were cured at 100° C. instead of the 120° C. of Example 1. Table II reports the results of the Knoop hardness test.

TABLE II

| Effect on Cure of HALS 5 and 6 | |
|---|---|
| HALS | KHN* |
| None | 5.6 |
| 1 | Tacky |
| 5 | 5.3 |
| 6 | 5.3 |

*Knoop Hardness No. (25 g wgt. - 10 × Power)

The data in Table II demonstrates that HALS 5 and 6 of this invention have little or no effect on the cure of the coating. However, in comparison, HALS 1 greatly affects the cure.

LIGHT STABILIZING EFFECTIVENESS

Example 3

Bonderite ®40 brand of cold rolled steel test panels, coated with a primer surfacer (PPG E5584) and a white base coat based on a thermosetting acrylic resin, were coated with the basic (clear) coating formulation used in Example 1. The basic coating formulations contained the stabilizers listed in tables III and IV. The coated test panels were subjected to weathering for 1,000 hours in a QUV accelerated weathering instrument. In this test, the samples were subjected to alternate cycles of UV light at 70° C. for 8 hours and a humid atmosphere with no UV light at 50° C. for 4 hours. Subsequently, the gloss of the surface was measured in accordance with ASTM D523.

The test results are reported in Tables III and IV.

TABLE III

| Light Stabilization Property with HALS 1 and 2 | |
|---|---|
| HALS | % 20° Gloss Retention |
| None | 0 |
| 1 | 84 |
| 2 | 92 |

TABLE IV

| Light Stabilization Property with HALS 5 and 6 | |
|---|---|
| HALS | % 20° Gloss Retention |
| None | 20 |
| 5 | 99 |
| 6 | 100 |

The data in Tables III and IV demonstrate that the HALS of this invention are effective light stabilizers.

What is claimed is:

1. A method of stabilizing an acid cured coating formulation against photo and/or thermal degradation without adverse effect on acid cure comprising incorporating in said coating formulation a stabilizing effective amount of a HALS represented by Formula I:

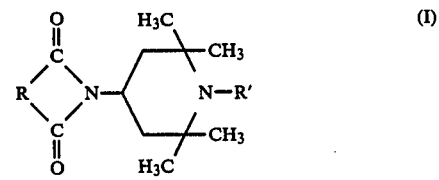

wherein R is a saturated or unsaturated, optionally alkyl- or alkenyl-substituted alkylene or cycloalkylene radical having 2-20 C-atoms and R' is selected from the group consisting of:

hydrogen;
an alkyl radical having 1–20 C-atoms;
an alkenyl radical having 3–5 C-atoms;
an aralkyl radical having 7–12 C-atoms;
—CH$_2$—CH$_2$—CN;
—CH$_2$—CH$_2$—COO—alkyl;
—CH$_2$—CH(CH$_3$)—COO—alkyl;
an acyl radical; and
—(CH$_2$—CH$_2$O)$_n$H, wherein n can be 1–10.

2. A method of claim 1 wherein from about 0.1 to about 5 wt. %, based on the weight of resin solids, of said HALS is used.

3. A method of claim 1 wherein R is selected from the group consisting of:

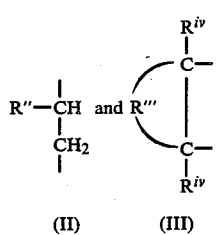

(II)         (III)

wherein R″ is selected from the group consisting of: (a) C$_{12}$–C$_{18}$ alkyl or alkylene; (b) cycloalkylene; (c) 1,2-cyclohexanediyl and methyl-substituted 1,2-cyclohexanediyl; and (d) bicyclic divalent radicals; R‴ is an alicyclic ring or ring system; and R$^{iv}$ is hydrogen or alkyl.

4. A method of claim 3 wherein R is selected from the group consisting of:

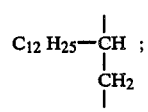         (XI)

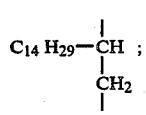         (XII)

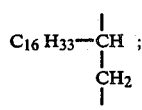         (XIII)

         (IIIa)

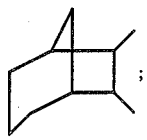         (IIIb)

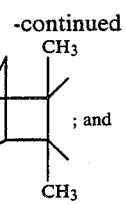         (IIIc)

; and

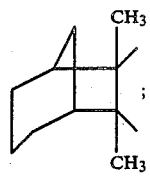         (IIId)

;

5. A method of claim 1 wherein R′ is —CH$_3$.

6. A method of claim 1 wherein R is selected from the group consisting of:

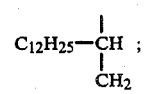         (XI)

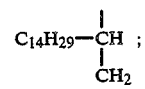         (XII)

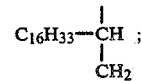         (XIII)

wherein R′ is —CH$_3$; and wherein about 0.1 to about 5 wt. %, based on the weight of resin solids, of said HALS is used.

7. A method of claim 6 wherein from about 0.5 to about 1.5 wt. %, based on the weight of resin solids, of said HALS is used.

8. An acid cured coating composition stabilized against photo and/or thermal degradation comprising a stabilizingly effect amount of a HALS represented by Formula I:

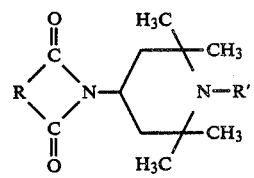         (I)

wherein R is a saturated or unsaturated, optionally alkyl- or alkenyl-substituted alkylene or cycloalkylene radical having 2–20 C-atoms and R′ is selected from the group consisting of:
hydrogen;
an alkyl radical having 1–20 C-atoms;
an alkenyl radical having 3–5 C-atoms;
an aralkyl radical having 7–12 C-atoms;
—CH$_2$—CH$_2$—CN;
—CH$_2$—CH$_2$—COO—alkyl;
—CH$_2$—CH(CH$_3$)—COO—alkyl;
an acyl radical; and
—(CH$_2$—CH$_2$O)$_n$H, wherein n can be 1–10.

9. A composition of claim 8 wherein from about 0.1 to about 5 wt. %, based on the weight of resin solids, of said HALS is used.

10. A composition of claim 8 wherein R is selected from the group consisting of:

$$R''-\underset{\underset{CH_2}{|}}{\overset{}{C}H} \quad \text{and} \quad R'''-\underset{\underset{R^{iv}}{|}}{\overset{\overset{R^{iv}}{|}}{C}-}\underset{R^{iv}}{\overset{}{C}-}$$

(II)     (III)

wherein R″ is selected from the group consisting of: (a) $C_{12}$–$C_{18}$ alkyl or alkylene; (b) cycloalkylene; (c) 1,2-cyclohexanediyl and methyl-substituted 1,2-cyclohexanediyl; and (d) bicyclic divalent radials; R‴ is an alicyclic ring or ring system; and $R^{iv}$ is hydrogen or alkyl.

11. A composition of claim 8 wherein R is selected from the group consisting of:

$$C_{12}H_{25}-\underset{\underset{CH_2}{|}}{\overset{}{C}H}\ ;$$

(XI)

$$C_{14}H_{29}-\underset{\underset{CH_2}{|}}{\overset{}{C}H}\ ;$$

(XII)

$$C_{16}H_{33}-\underset{\underset{CH_2}{|}}{\overset{}{C}H}\ ;$$

(XIII)

(IIIa)

(IIIb)

(IIIc)

(IIId)

12. A composition of claim 8 wherein R′ is —$CH_3$.

13. A composition of claim 8 wherein R is selected from the group consisting of:

$$C_{12}H_{25}-\underset{\underset{CH_2}{|}}{\overset{}{C}H}\ ;$$

(XI)

$$C_{14}H_{29}-\underset{\underset{CH_2}{|}}{\overset{}{C}H}\ ; \text{and}$$

(XII)

$$C_{16}H_{33}-\underset{\underset{CH_2}{|}}{\overset{}{C}H}$$

(XIII)

wherein R′ is —$CH_3$; and wherein about 0.1 to about 5 wt. %, based on the weight of resin solids, of said HALS is used.

14. A composition of claim 13 wherein from about 0.5 to about 1.5 wt. %, based on the weight of resin solids, of said HALS is used.

15. A composition of claim 8 wherein from about 0.5 to about 1.5 weight percent, based on the weight of resin solids, of said HALS is used.

16. A composition of claim 8 which retains at least about 86% of its hardness after cure, wherein said hardness is measured on the Knoop hardness scale.

17. A method of stabilizing an acid cured resin containing coatings formulation, wherein the resin is selected from the group consisting of acrylic resins, melamine resins, and mixtures thereof, against photo and/or thermal degradation without adverse effect on acid cure, said process comprising incorporating in said coating formulation a stabilizingly effective amount of a HALS represented by Formula I:

(I)

wherein R is a saturated or unsaturated, optionally alkyl- or alkenyl-substituted alkylene or cycloalkylene radical having 2–20 C-atoms and R′ is selected from the group consisting of:
hydrogen;
an alkyl radical having 1–20 C-atoms;
an alkenyl radical having 3–5 C-atoms;
an aralkyl radical having 7–12 C-atoms;
—$CH_2$—$CH_2$—CN;
—$CH_2$—$CH_2$—COO—alkyl;
—$CH_2$—$CH(CH_3)$—COO—alkyl;
an acyl radical; and
—$(CH_2$—$CH_2O)_nH$, wherein n can be 1–10.

* * * * *